United States Patent [19]

James

[11] 4,368,323
[45] Jan. 11, 1983

[54] SUBSTANTIVE WETTING AGENTS FOR ABSORBENT MATERIALS

[75] Inventor: Richard P. James, Cranbury, N.J.

[73] Assignee: Personal Products Company, Milltown, N.J.

[21] Appl. No.: 303,752

[22] Filed: Sep. 21, 1981

[51] Int. Cl.³ .................... A61F 13/16; A61F 13/20; C08B 11/00

[52] U.S. Cl. .................................... 536/56; 128/285; 128/290 R; 128/296; 162/72; 162/92; 525/61; 536/57; 536/87; 536/88

[58] Field of Search ........................ 536/56, 87, 88, 57; 128/285, 290 R, 296; 525/61; 162/72, 92

[56] References Cited

U.S. PATENT DOCUMENTS

| | | | |
|---|---|---|---|
| 2,710,861 | 6/1955 | Charles et al. | 536/56 |
| 3,936,441 | 2/1976 | Holst et al. | 536/57 |
| 3,959,080 | 5/1976 | Orth et al. | 536/88 |
| 3,971,379 | 7/1976 | Chatterjee | 128/285 |
| 4,020,271 | 4/1977 | Chatterjee | 128/285 |
| 4,250,306 | 2/1981 | Lask et al. | 536/88 |
| 4,305,393 | 12/1981 | Nguyen | 128/285 |
| 4,318,408 | 3/1982 | Korpman | 128/285 |

*Primary Examiner*—Ronald W. Griffin
*Attorney, Agent, or Firm*—Jason Lipow

[57] ABSTRACT

The absorbent material is treated to increase its wettability in a substantive manner. This is accomplished by reacting a diepoxide compound with an absorbent material selected to have accessible hydroxyl groups and with a surfactant having functional end groups selected from the group consisting of primary amine or hydroxyl groups.

11 Claims, No Drawings

SUBSTANTIVE WETTING AGENTS FOR ABSORBENT MATERIALS

BACKGROUND OF THE INVENTION

This invention relates to providing absorbent materials with increased wettability and specifically providing this property of increased wettability in a permanent or substantive manner.

Commonly available absorbent materials such as rayon, cotton, and chemical wood pulp have been used as the raw materials for many commercial absorbent products including, for example, such products for absorbing body fluids as catamenial napkins and tampons, diapers, and surgical dressings. While in the main, such commonly available absorbents have proven useful in such products, in an effort to improve product quality and economy, the art has searched for improved materials. Recently, it has been proposed that the more traditionally employed absorbent materials be, at least in part, substituted for with less expensive absorbents. Examples of these are the relatively inexpensive wood pulps such as thermechanical wood pulp, mechanical wood pulp, and refiner pulp. Further, such non wood pulp absorbents as for example, peat moss and various grasses have been considered. Unfortunately, while these materials have the advantage of reduced cost and are all readily available, they have suffered from the common problem of poor initial wettability as is required for use in body fluid absorbing products.

To correct this deficiency, it is known that certain surface active agents may be applied to these absorbents to provide good re-wetting properties. These agents are typically characterized by the presence of hydrophilic groups in the middle of a hydrophobic chain or as viscus liquids or waxy solids. Such surface active agents are generally classified as cationic agents, anionic agents, nonionic agents, and are all capable of greatly increasing the wettability of the absorbents to which they are applied. Examples of such agents are the alkyl phenols containing sixty to seventy percent polyoxyethylene, alkylsulfosuccinates, and sulfated esters.

Accordingly, surface active agents are known which can greatly enhance the wettability of absorbents and so make them useful in commercial products, it is unfortunate that, heretofore, the surface active agents have lacked the property of substantivity. Said in other words, these agents have not been permanently associated with the absorbent material and as a result have tended to wash out of the material, either during the processing or in use. Accordingly, in a short time, they lose their effectiveness thereby frustrating the purpose of their employment. There is a need, therefore, for a method of providing absorbents with the property of wettability which property is of a permanent or substantive nature.

SUMMARY OF THE INVENTION

It has now been discovered that an absorbent of the type having accessible hydroxyl group, may be provided with the property of wettability and that this property may be rendered substantive. Specifically, it has been discovered that such an absorbent may be provided with increased substantive wettability by reacting the absorbent, in the presence of a diepoxide, with a surfactant having functional end groups selected from the group consisting of primary amine or hydroxyl groups. The surfactant will form cross links with the absorbent and itself, with the diepoxide serving as a bridging or cross linking agent.

In particular, the preferred surfactant has the general formula:

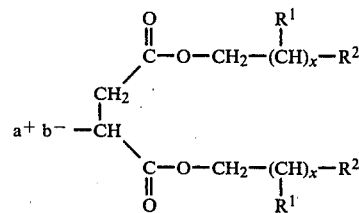

wherein $a^+$ is selected from the group consisting of alkali metal ion or $NH_4+$; $b^-$ is selected from the group consisting of $SO_3-$, $SO_4-$, or $HPO_3-$; $-R^1$ and $-R^2$ are each independently selected from the group consisting of $-H$, $-OH$, $-CH_2OH$ or $-NH_2$ and x is a whole number of from 0 to 6.

In accordance with the method of this invention, the diepoxide forms ether linkages with the accessible hydroxyl groups of the absorbent and covalent bonds with the functional end groups of the surfactant. Preferably, the diepoxide is butadiene diepoxide. The absorbent may be selected from the group consisting of wood pulp, regenerated cellulose, grass pulp, peat moss, or other non-cellulosic absorbent substrates which contain hydroxyl groups receptive to such cross linking such as, for example, the newly developed synthetic wood pulp or polyvinyl alcohol fibers. Preferably, the substrate of choice is cellulose derived from such wood sources as chemical wood pulp, mechanical wood pulp, refiner wood pulp, or thermomechanical wood pulp.

DETAILED DISCUSSION OF THE INVENTION

In accordance with this invention, a surfactant having functional end groups is reacted together with an absorbent having accessible hydroxyl groups and a diepoxide compound to produce an absorbent with durable wettability.

The surfactant is essentially a substituted wetting agent and, specifically, a wetting agent which has been substituted with primary amine or hydroxyl groups. The wetting agent of choice is a sulfosuccinate surfactant wherein the ester groups are substituted with amine and/or hydroxyl groups. Such substituted wetting agents will have the general formula:

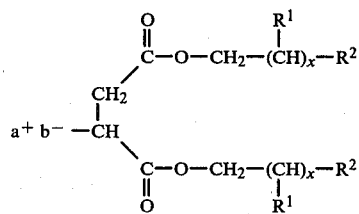

wherein $a^+$ is selected from the group consisting of alkali metal ion or $NH_4-$; $b^-$ is selected from the group consisting of $SO_3-$, $SO_4-$, or $HPO_3-$; $-R^1$ and $-R^2$ are each independently selected from the group consisting of $-H$, $-OH$, $-CH_2OH$ or $-NH_2$ and x is a whole number of from 0 to 6.

The substituted surfactants may be produced by reacting maleic anhydride with lower alkyl alcohols which may also contain halide and/or amine groups such as, for example, 2-chloro-ethanol, glycerol, 2-aminoethanol, 4-aminobutanol, 1,4-butanediol and the like, to form the corresponding diester. The reaction may be carried out at a high temperature, e.g., at reflux temperature in a suitable solvent such as toluene, and may require from about 1 to 10 hours for substantial completion. The degree of conversion of the reactants to the diester may be enhanced by the removal of water from the reaction vessel. The diester is then isolated from the reaction mixture by such means as distillation or precipitation of the resulting product when such product is insoluble in the reaction mixture. Halide groups associated with diester are preferably converted to amines by reacting with an ammonium hydroxide solution and then neutralizing with a strong base. The diester is next reacted with an inorganic salt which may be, for example, the alkali metal or ammonium salt of sulfuric, sulfurous or phosphoric acid. This reaction is carried out by heating the diester together with the inorganic salt in a water solution of the salt to form the substituted surfactants employed in this invention.

The substituted wetting agents of choice are substituted sodium dialkysulfosuccinate and specifically sodium di-2-aminoethylsulfo-succinate and sodium di-2,3-dihydroxypropylsulfosuccinate. The following are illustrative of the synthesis of these substituted wetting agents:

SYNTHESIS OF SODIUM DI-2-AMINOETHYLSULFOSUCCINATE

Maleic anhydride is reacted with 2-chloroethanol. This is accomplished by refluxing 0.2 moles of anhydride with 0.4 moles of the 2-chloroethanol in 200 cc's of toluene for 7 hours in a refluxing apparatus fitted with a Dean-Stark tube to trap the evolved water. Approximately fifty-five percent of the reagents produce the diester, di-2-chloroethylmaleate (compound A). Toluene is then removed by distillation. The reaction product, compound A, is then reacted with an excess of concentrated ammonium hydroxide (e.g., one mole), for ninety hours at room temperature to yield the di-2-ethylaminehydrochloride ester of maleic acid (compound B). Excess ammonia is evaporated using a steam bath. Sodium hydroxide (0.4 moles) are dissolved in 50 cc's of distilled water and reacted with Compound B to give the free amine (compound C). The neutralization reaction is allowed to go for 70 hours. Compound C is reacted in a solution of 50 cc's of distilled water and 0.2 moles of sodium bisulphite for 13 hours on a steam bath to yield the sodium di-2-amino ethysulfosuccinate.

SYNTHESIS OF SODIUM DI-2,3-DIHYDROXYPROPYLSULFOSUCCINATE

Maleic anhydride in a quantity of 0.2 moles is reacted with 0.4 moles of glycerol by reflexing together in 200 cc's of toluene for 14 hours in a refluxing apparatus fitted with a Dean-Stark tube to trap evolved water. Approximately ninety percent of these reagents are converted to di-2,3-dihydroxypropylmaleate (compound A). It will be understood that because glycerol has three reactive hydroxyl groups, the resulting reaction forms a mixture of products. For clarity, however, only compound A is referred to. Compound A is reacted with a solution of 0.2 moles of sodium bisulfite in 50 cc's of distilled water for 15 hours on a steam bath to yield sodium di-2,3-dihydroxypropylsulfosuccinate.

In accordance with the invention, the substituted wetting agents are reacted with an absorbent having accessible hydroxyl groups in the presence of a diepoxide. The diepoxide serves the function of forming bridges between the wetting agent and the absorbent and in this sense acts as a cross linking agent. By accessible hydroxyl group it is meant such groups which are capable of forming ether linkages with the diepoxide. It is also possible to form branch compounds of the wetting agent or to cross link the absorbent per se. Generally, the diepoxide serves to perform all three functions and produces mixtures of these reaction products. The diepoxide of choice is butadiene diepoxide.

A wide variety of absorbent materials having accessible hydroxyl groups may be given enhanced wettability by following the teachings of this invention. Cellulose and any cellulose containing natural products such as those found in wood, cotton, grasses, or peat moss may all be given improved substantive wettability by the method taught herein. Additionally, such man-made cellulosics such as regenerated cellulose or chemically modified cellulosics or starches may also be employed. The teachings of this invention are particularly useful for certain absorbent materials which have the great advantage of being inexpensive but which suffer from the drawbacks of poor wettability. Specifically, such materials are the mechanical wood pulps and peat moss. Mechanial wood pulp is meant to include such materials as ground wood pulp, refiner wood pulp, or thermomechanical wood pulp. Ground wood pulp is essentially trees and branches which have been debarked, cleaned, and then ground into particulate matter. Refiner wood pulp differs from ground wood pulp only in that the grinding step utilized is a refiner, i.e., a disk-like device known in the art which may be described generally as having metallic ribs at the peripheral sections thereof which last contact the wood particles and help to separate the wood fibers without excessively damaging them. Thermomechanical wood pulp is similar to refiner wood pulp with the exception that the wood particles are heated when in the refiner, usually with steam, and this heating further aides in separating the wood fibers. The common characteristic of these mechanical pulps is that no attempt has been made to separate the fibers by chemical means although of course they may, after having been reduced to fibrous or finer particulate matter, be subjected to chemical treatment, e.g., bleaching, for example. Because of this lack of chemical treatment during the defibration step, these fibers have adhered to them such non-wettable materials such as lignin, and hemi-cellulose. It is because of this that the methods of this invention are particularly useful in connection with these materials and will enhance the wettability of these fibers in a substantive manner.

Peat moss is yet another inexpensive, cellulose containing absorbent material which can benefit from the treatment described herein. Basically, peat moss is a combination of celluloses, lignins, and humic acids. While this material has good absorbent properties because of the particular leafy structure of the peat moss, dry peat moss does not initially exhibit good wettability. By incorporating the teachings herein, substantive wetting agents may be incorporated into the peat moss structure thereby rendering the peat moss highly wettable and increasing its use as an economical absorbent.

Additionally, certain synthetic polymer materials may be used as the absorbent material to be treated in accordance with this invention. It is known, for example, to employ as absorbents, the so-called synthetic wood pulp materials which are fibers formed from polyolefins e.g., polyethylene and polypropylene, such as those sold by the Crown Zellerbach corporation of Nevada, under the trademark, SWP. Such polyolefins have incorporated therein to impart a degree of hydrophilicity, small quantities of poly(vinyl alchohol). The poly(vinyl alchohol) in these fibers provide the accessible hydroxyl groups to which, in accordance with this invention, the diepoxide bridging agents may be bonded by ether linkages. Still another example of absorbent materials benefited by the teachings herein could be for example poly(vinyl alcohol) fibers which have been also suggested for use as an absorbents.

The substituted wetting agents, the diepoxide, and the absorbent material are all reacted together, preferably in the presence of a catalyst, to produce the cross linked products of this invention. A suitable catalyst is, for example, benzyl dimethyl amine.

The reaction can be carried out at room temperature by slurrying the absorbent material in a solution containing the substituted surfactant and the diepoxide. Water is a suitable solvent. The reaction is enhanced by elevated temperatures such as up to the normal boiling point of the solvent. The elevated temperatures may be imposed by heating the slurry of the reactants. Alternatively, the reaction may be carried out by drying off the solvent and heating the residue or by simultaneously heating the slurry and drying off the solvent.

It is believed that as a result of this reaction, the hydroxyl groups of the absorbent form ether linkages with the diepoxide reactant. Also, the diepoxide reacts with the substituted surfactants to form ether linkages or secondary amines depending on the functional groups; i.e., hydroxyl or amine.

EXAMPLE 1

A water solution comprising 200 cc of water, 0.1 grams of sodium di-2,3-dihydroxypropylsulfosuccinate and 0.1 grams of butadienediepoxide is prepared. Additionally, dissolved into the solution is 0.001 grams of benzyl dimethyl amine catalyst. A quantity of thermomechanical wood pulp, equal to 20 grams, is slurried into the solution and the mixture is allowed to react after stirring for several minutes. Water is evaporated from the system by allowing the system to stand over night and the resulting treated thermomechanical wood pulp is air dried in an oven. The so treated thermomechanical wood pulp exhibits far more wettability than the untreated materials and such wettable properties survive even after the thermomechanical wood pulp has been thoroughly washed in distilled water.

EXAMPLE 2

The procedure of Example 1 is followed with the exception that a sample is prepared using the solution containing only the butadiene diepoxide. A second sample is prepared using only the substituted surfactants in the quantity of 0.1 grams of surfactant to 200 cc of water. A third sample is prepared using a solution containing only 0.1 grams of diepoxide and 0.1 grams of surfactant in 200 cc of water. Each of these three samples are tested for wettability along with the thermo mechanical wood pulp which has been treated in accordance with Example 1 and a sample of totally untreated thermo mechanical wood pulp. The test comprises thoroughly washing the air dried pulp undergoing the various treatments with distilled water and then testing the washed material using the Basket Sink Test Method. In accordance with this test method, the relative rate of absorption of various pulp samples may be compared to each other by placing such samples in a wire basket which is then dropped into a container of water. The time required for the basket to sink is measured; the greater the time, the less wettable the wood pulp. The results of testing the various samples are reported in Table 1 below.

TABLE 1

| Sample | Basket Sink Time (Sec) |
| --- | --- |
| Thermomechanical wood pulp (TMP) untreated | 126 |
| TMP with diepoxide | 96 |
| TMP with surfactant | 98 |
| TMP with surfactant and diepoxide | 100 |
| TMP with surfactant, diepoxide, and catalyst | 74 |

As can be seen from the above data, the thermomechanical wood pulp is relatively non wettable per se. The addition of certain ingredients such as diepoxides or surfactants reduce the sink time and hence increase the wettability to a minor degree. It is only when the entire reaction system is present, i.e., the diepoxide, the surfactant and the catalyst that substantial and lasting reduction in the sink time (or increase in wettability) is accomplished.

What is claimed is:

1. A method for treating an absorbent material having accessible hydroxyl groups to increase wettability comprising reacting said absorbent material with a surfactant having functional end groups selected from the group consisting of primary amine or hydroxyl groups and a diepoxide compound.

2. The method of claim 1 wherein said surfactant has the general formula:

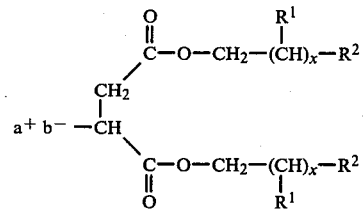

wherein $a^+$ is selected from the group consisting of alkali metal ion or $NH_4+$; $b^-$ is selected from the group consisting of $SO_3-$, $SO_4-$, or $HPO_3-$; $-R^1$ and $-R^2$ are each independently selected from the group consisting of $-H$, $-OH$, $-CH_2OH$ or $-NH_2$ and x is a whole number of from 0 to 6.

3. The method of claim 1 wherein said diepoxide is butadiene diepoxide.

4. The method of claim 1 wherein said diepoxide forms ether linkages with said accessible hydroxyl groups of the absorbent material and covalent bonds with said functional end groups of the surfactant.

5. The method of claim 1 wherein said absorbent material is selected from the group consisting of wood pulp, regenerated cellulose or peat moss.

6. The method of claim 1 wherein said absorbent material is cellulose.

7. The method of claim 6 wherein said cellulose is selected from the group consisting of chemical wood pulp, thermomechanical wood pulp, or mechanical wood pulp.

8. The method of claim 1 wherein said surfactant is a sulfosuccinate compound wherein the ester groups thereof are substituted with amine groups.

9. The method of claim 8 wherein said surfactant is sodium di-2-aminoethylsulfosuccinate.

10. The method of claim 1 wherein said surfactant is a sulfosuccinate surfactant wherein the ester groups are substituted with hydroxyl groups.

11. The method of claim 10 wherein said surfactant is sodium di-2,3-dihydroxypropylsulfosuccinate.

* * * * *